(12) United States Patent
Schubert et al.

(10) Patent No.: US 10,244,967 B2
(45) Date of Patent: Apr. 2, 2019

(54) METHOD AND APPARATUS FOR DETERMINING DIFFERENCES IN GEOMETRY OF SUBJECT ELEMENT USING LANDMARKS

(71) Applicant: Brainlab AG, Munich (DE)

(72) Inventors: Mario Schubert, Poing (DE); Melanie Wegner, Kirchseeon (DE); Sabine Kling, Unterschleissheim (DE); Luise Poitzsch, Oberding (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/617,793

(22) Filed: Jun. 8, 2017

(65) Prior Publication Data

US 2018/0085032 A1  Mar. 29, 2018

Related U.S. Application Data

(63) Continuation of application No. 14/773,553, filed as application No. PCT/EP2013/069358 on Sep. 18, 2013, now abandoned.

(51) Int. Cl.
*A61B 5/00* (2006.01)
*A61B 5/107* (2006.01)
(Continued)

(52) U.S. Cl.
CPC .......... *A61B 5/1079* (2013.01); *A61B 5/0077* (2013.01); *A61B 5/1072* (2013.01);
(Continued)

(58) Field of Classification Search
CPC ............... A61B 19/50; A61B 19/5244; A61B 2019/461; A61B 5/0077; A61B 5/1072;
(Continued)

(56) References Cited

U.S. PATENT DOCUMENTS 5,700,268 A  12/1997  Berlin
6,027,507 A   2/2000  Anderson et al.
(Continued)

FOREIGN PATENT DOCUMENTS

WO  00/32093  6/2000
WO  01/30247  5/2001
(Continued)

OTHER PUBLICATIONS

International Search Report and Written Opinion from corresponding International Application No. PCT/EP2013/069358 dated Dec. 9, 2013.
(Continued)

*Primary Examiner* — Max F Hindenburg
(74) *Attorney, Agent, or Firm* — Middleton Reutlinger

(57) ABSTRACT

A method, performed by a computer, for measuring geometric length and offset differences of a subject element using landmarks obtained through, for example, analysis of medical data images. The method may include obtaining medical image data from a medical imaging device. The method includes measuring, by the computer, a first landmark vector between a femoral landmark and a second landmark at a first point in time from, for example, the medical data images. Further, the method includes measuring, by the computer, a second landmark vector between the femoral landmark and the second landmark at a second point in time which is later than the first point in time from, for example, the medical data images. Calculating an orthogonal projection of the first landmark vector into a sagittal plane and using the direction of the orthogonal projection of the first landmark vector into the sagittal plane as a length direction. Calculating a direction which is perpendicular to the sagittal plane and using this direction as an offset direction and calculating the length difference in the length
(Continued)

Figure 1:
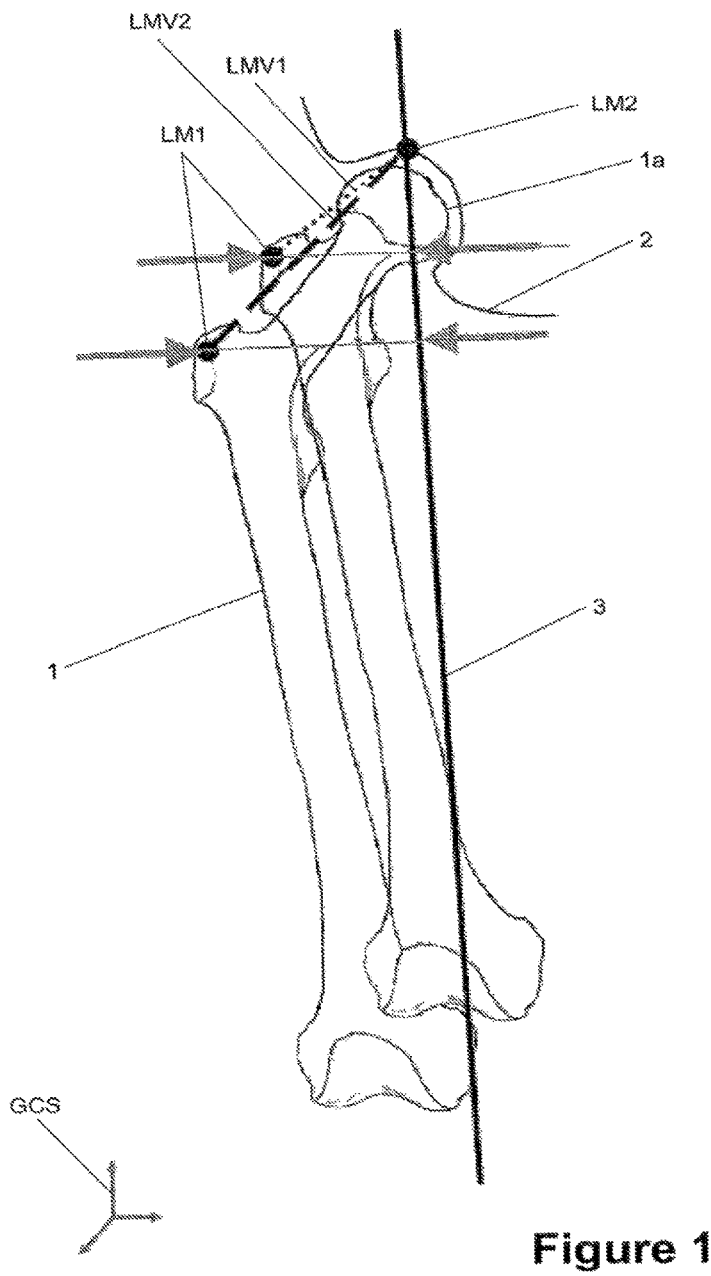

direction and the offset difference in the offset direction from the first landmark vector and the second landmark vector.

15 Claims, 7 Drawing Sheets

(51) Int. Cl.

| | | |
|---|---|---|
| A61B 5/11 | (2006.01) | |
| G01B 11/14 | (2006.01) | |
| G06K 9/52 | (2006.01) | |
| G06T 3/60 | (2006.01) | |
| G06T 7/00 | (2017.01) | |
| G06T 7/60 | (2017.01) | |
| A61B 34/20 | (2016.01) | |
| G06T 7/30 | (2017.01) | |
| G06T 7/73 | (2017.01) | |
| G06F 19/00 | (2018.01) | |
| A61B 90/00 | (2016.01) | |

(52) U.S. Cl.
CPC .......... *A61B 5/1075* (2013.01); *A61B 5/1121* (2013.01); *A61B 5/1127* (2013.01); *A61B 5/4538* (2013.01); *A61B 5/7278* (2013.01); *A61B 34/20* (2016.02); *G01B 11/14* (2013.01); *G06F 19/00* (2013.01); *G06K 9/52* (2013.01); *G06T 3/60* (2013.01); *G06T 7/0014* (2013.01); *G06T 7/30* (2017.01); *G06T 7/60* (2013.01); *G06T 7/73* (2017.01); *G06T 7/74* (2017.01); *A61B 2034/2048* (2016.02); *A61B 2034/2055* (2016.02); *A61B 2034/2068* (2016.02); *A61B 2090/3937* (2016.02); *A61B 2562/0219* (2013.01); *A61B 2576/00* (2013.01); *G06T 2207/30004* (2013.01); *G06T 2207/30204* (2013.01)

(58) Field of Classification Search
CPC ... A61B 5/1075; A61B 5/1121; A61B 5/4538; A61B 5/7278; A61B 5/1079
See application file for complete search history.

(56) References Cited

U.S. PATENT DOCUMENTS

| | | |
|---|---|---|
| 7,001,346 B2 | 2/2006 | White |
| 2003/0105470 A1 | 6/2003 | White |
| 2008/0146969 A1 | 6/2008 | Kurtz |
| 2011/0009285 A1 | 4/2011 | Burger |
| 2011/0092858 A1* | 4/2011 | Burger ................... A61B 34/10 600/587 |
| 2012/0283599 A1 | 11/2012 | Santiago |
| 2013/0085723 A1* | 4/2013 | Chabanas ............... G06T 17/00 703/1 |
| 2016/0022173 A1* | 1/2016 | Schubert .............. A61B 5/1127 600/587 |

FOREIGN PATENT DOCUMENTS

| | | |
|---|---|---|
| WO | 2004069073 | 8/2004 |
| WO | 2006119776 | 11/2006 |
| WO | 2006128301 | 12/2006 |
| WO | 2007095248 | 8/2007 |
| WO | 2009040537 | 4/2009 |
| WO | 2009062314 | 5/2009 |
| WO | 2009106812 | 9/2009 |
| WO | 2012080840 | 6/2012 |

OTHER PUBLICATIONS

Renkawitz et al., "Leg Length and Offset Measures with a Pinless Femoral Reference Array during THA", Clinical Orthopaedics and Related Research, vol. 468, No. 7, Sep. 2009, pp. 1862-1868.
Zheng et al., "A hybrid CT-free navigation system for total hip arthroplasty", Computer Aided Surgery, vol. 7, No. 3, Jan. 2002, pp. 129-145.

* cited by examiner

METHOD AND APPARATUS FOR DETERMINING DIFFERENCES IN GEOMETRY OF SUBJECT ELEMENT USING LANDMARKS

The present invention relates to a data processing method, a software program and an apparatus for determining a leg length difference and a leg offset difference of a patient's leg including a femur, a tibia and a knee, wherein the leg is connected to a pelvis via a hip joint.

Some events, such as an accident or surgery, can change the geometry of the leg and in particular the geometry of the femur. In such cases, it is desirable to be able to compare the geometry before and after the event. A leg length difference and/or leg offset difference are of particular interest. The leg length difference is the difference in the length of the leg before and after the event and is typically measured in a direction of the mechanical axis of the femur, which is identical or approximate to a sagittal, superior-inferior or cranial-caudal direction. The leg offset difference is the change or displacement of the leg in a lateral direction. The leg length difference is given in a leg length difference direction, and the leg offset difference is given in a leg offset direction, wherein the leg length difference direction and the leg offset direction are in particular orthogonal to each other.

An overview of some of the terms used in this document shall now be given in order to render the rest of the document more comprehensible.

A landmark is typically a defined element of an anatomical body part which is preferably always identical or recurs with a high degree of similarity in the same anatomical body part of multiple patients. A landmark can be a natural landmark which can be easily determined, in particular sampled using a pointer or any other suitable device. Typical natural landmarks are for example the epicondyles of a femoral bone. A landmark can however also be an artificial landmark, such as for example a particular structure which is rigidly attached to the anatomical body part, such as for example a screw. A landmark can also be a virtual landmark which cannot be directly sampled but can be determined indirectly. An example of a virtual landmark is the centre of rotation of the femur, which is in particular the centre of the femoral head.

The position of an object or a point, i.e. its spatial location in up to three spatial dimensions and/or its alignment in up to three rotational dimensions, is preferably determined in a global co-ordinate system. Examples of a global co-ordinate system include an earth-fixed co-ordinate system which can be defined by parameters such as a gravity vector and the magnetic field of the earth, and an artificial global co-ordinate system which can be defined by field generators which generate a magnetic and/or electric field.

A reference point is a point with a static position in a particular co-ordinate system, in particular in the global co-ordinate system. A landmark reference vector is a vector between a landmark and the reference point. A landmark vector is a vector between two landmarks and can be acquired directly or can be calculated from two landmark reference vectors. The two landmarks and the reference point either lie on the same line or constitute the corners of a triangle, hence if the two landmark reference vectors between the reference point and the respective landmarks are known, the landmark vector between the two landmarks can be unambiguously calculated.

The term "direction" means the alignment or orientation of a line in which a vector lies. The direction of a vector from a first point to a second point is unambiguous, while the direction of a vector between a first point and a second point is ambiguous because it can be the direction from the first point to the second point or the direction from the second point to the first point. However, this ambiguity is irrelevant as long as it is resolved for any calculation where necessary. A vector has a direction and a magnitude, which means the vector's length.

In standard navigated procedures, the leg length difference and the leg offset difference are determined using markers which are attached to the femur and the pelvis. The positions of the markers, and therefore of the femur and the pelvis, are tracked using a medical navigation system. One popular implementation of a medical navigation system uses a stereoscopic camera which captures an image of a marker. The medical navigation system determines the absolute position of the pelvis and the femur in a particular co-ordinate system and calculates the positional relationship between them. The inventors of the present invention have found a different approach for determining the leg length difference and the leg offset difference which does not require attaching markers to the femur and the pelvis.

In a brief summary, which is not to be understood as limiting the present invention in any way, it may be said that this approach analyses the vector between two landmarks at different points in time. This so-called landmark vector can be acquired directly or can be calculated from vectors between the respective landmarks and a common reference point, for example for an easy integration into the surgical procedure. A landmark reference vector is in particular determined from the orientation of a laser beam which is aimed at a particular point, wherein the position of the laser beam source relative to the landmark is known, for example by being measured. The point at which the laser beam is directed is either the common reference point or an offset point with a known location relative to the common reference point.

The present invention is defined by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. In particular, a feature of one embodiment which has the same or a similar function to another feature of another embodiment can be exchanged with said other feature. In particular, a feature of one embodiment which adds an additional function to another embodiment can be added to said other embodiment.

The present invention relates to a method for determining a leg length difference and a leg offset difference of a patient's leg including a femur. The method comprises the steps of: determining a first landmark vector between a femoral landmark and a second landmark at a first point in time; and determining a second landmark vector between the (identical or same) femoral landmark and the (identical or same) second landmark at a second point in time which is later than the first point in time. The first and second landmark vectors represent the positional relationship between the two points (the femoral landmark and the second landmark) at two different points in time. The difference between the two landmark vectors therefore represents a change in the geometry of the patient's leg. The leg length difference and the leg offset difference (between the first and second points in time) can thus be determined by appropriately analysing the two landmark vectors, in particular by decomposing the difference between the two landmark vectors into at least the leg length direction and the leg offset direction.

The method further comprises the step of calculating an orthogonal projection of the first landmark vector into a sagittal plane and using the direction of the orthogonal projection of the first landmark vector into the sagittal plane as the leg length direction. The leg length direction is assumed to lie within a sagittal plane, such that a lateral component of the first landmark vector can be ignored by performing the projection.

In an orthogonal projection, a perpendicular is dropped onto a plane or line—in this case, the sagittal plane. In other words, the orthogonal projection of a point onto a plane or line is the point on the plane or line which has the shortest distance from the point to be projected.

The method further comprises the steps of calculating a direction which is perpendicular to the sagittal plane and using this direction as a leg offset direction; and calculating the leg length difference in the leg length direction and the leg offset difference in the leg offset direction from the first landmark vector and the second landmark vector.

The femoral landmark is preferably a point on the greater trochanter of the femur. The second landmark is preferably either a point on the pelvis, for example a point on the acetabular rim, or a landmark in a fix relation to the pelvis, such as a landmark which coincides with the centre of rotation of the femoral head.

The direction of a vector or a line is preferably defined in a global co-ordinate system. Examples of a global co-ordinate system include an earth-fixed co-ordinate system which can be defined by parameters such as the gravity vector and the magnetic field of the earth, and an artificial global co-ordinate system which can be defined by field generators which generate a magnetic and/or electric field.

It should be noted that a landmark may be accessed through the skin without any surgical intervention. If a surgical intervention is required in order to access a landmark, then this surgical intervention is performed in an independent, preceding step which is not part of the present invention. The present invention preferably only relates to processing the data obtained by sampling and not necessarily to the sampling process itself.

A major advantage of the present invention is that there is no need to acquire the absolute position of the landmarks in a co-ordinate system such as the global co-ordinate system. This would require an adequate medical navigation system, which is elaborate and expensive. In addition, a medical navigation system based on a stereoscopic camera needs an unobstructed field of view in order to capture stereoscopic images of a marker. The present invention only requires directions and distances, which can be acquired using simple sensors. The line-of-sight problem is reduced considerably as sources and sensors are brought closer together.

This invention requires the orientation of the sagittal plane to be known. In accordance with a first option, the sagittal plane is defined as a horizontal plane. This is an appropriate assumption if the patient is in a lateral recumbent position.

In accordance with a second option, the orientation of the sagittal plane is determined as the orientation of a surface of an operating table on which the patient is located. This is also based on the assumption that the patient is in a lateral recumbent position on the operating table. However, if the surface of the operating table is not horizontal, then the sagittal plane of the patient is also not horizontal. Since it is an appropriate assumption that the sagittal plane is parallel to the surface of the operating table, the orientation of the surface of the operating table can be used as the orientation of the sagittal plane. The orientation of the surface of the operating table is preferably determined using an orientation sensor such as an inertial sensor. In this document, an inertial sensor is capable of determining its orientation in up to three rotational dimensions, for example in a known reference system such as the global co-ordinate system.

In accordance with a third option, the sagittal plane is determined from a plurality of inertial sensor data which are acquired from an inertial sensor attached to the tibia of the leg while the femur is locked in position, preferably in its neutral position, and the tibia is flexed relative to the femur. If the tibia is flexed relative to the corresponding femur about the knee joint, the tibia moves within a plane which is parallel to the sagittal plane. If the sensor data provided by the inertial sensor are sampled for a plurality of positions of the tibia, then the orientation of the plane in which the tibia moves can be calculated.

In one embodiment, a first sagittal plane is determined for the first landmark vector, and a second sagittal plane is determined for the second landmark vector. The orthogonal projections of the landmark vectors into the corresponding sagittal plane are calculated. This embodiment is particularly useful if the orientation of the patient has changed, in particular relative to the global co-ordinate system. In this case, the leg length direction and the leg offset direction at the first point in time and second point in time are different. This is compensated for by projecting the first landmark vector into the first sagittal plane and the second landmark vector into the second sagittal plane, in order to determine the respective leg length directions and leg offset directions. The two sagittal planes are preferably co-registered in order to harmonise the leg length directions and the leg offset directions and so incorporate the first and second landmark vectors into the same reference system.

In one embodiment, calculating the leg length difference and the leg offset difference involves calculating a first orthogonal projection of the second landmark vector into the sagittal plane and calculating a second orthogonal projection of the first orthogonal projection of the second landmark vector onto the projection of the first landmark vector into the sagittal plane. This compensates for an anterior-posterior shift of the femur between the first and second points in time. Such an anterior-posterior shift occurs in the sagittal plane, perpendicular to the leg length direction.

The leg length difference is then determined as the difference in length between the projection of the first landmark vector into the sagittal plane and the second projection of the second landmark vector. The leg offset difference is then calculated as the difference between the components of the first landmark vector and the second landmark vector in the leg offset direction, which is the direction perpendicular to the sagittal plane.

In another embodiment, calculating the leg length difference and the leg offset difference involves calculating an orthogonal projection of the second landmark vector into the sagittal plane and rotating the orthogonal projection of the second landmark vector within the sagittal plane such that its direction matches the direction of the projection of the first landmark vector into the sagittal plane. This also compensates for an anterior-posterior shift of the femur between the first and second points in time as in the previous embodiment, but uses a rotation rather than a projection in order to align the two projections of the two landmark vectors. The leg length difference and the leg offset difference are then determined as in the previous embodiment.

In the previous embodiments, the two landmark vectors are decomposed into their components in the leg length direction and leg offset direction before the leg length difference and leg onset difference are calculated from these components. In another embodiment, calculating the leg length difference and the leg offset difference involves calculating the difference vector between the first landmark vector and the second landmark vector. This difference vector is then decomposed into its components in the leg length direction and the leg offset direction. In other words, the difference vector between the two landmark vectors is decomposed into the desired directions, whereas in the previous embodiment, the landmark vectors are first decomposed into the desired directions and the desired distances are then calculated from the difference between the corresponding components.

In one embodiment, neutral position data are obtained which define (or correspond to) a neutral position of the leg, and therefore of the femur, at the first point in time. Preferably, the neutral position data represent the orientation of the femur when it is in its neutral position. In particular, the leg is positioned in its neutral position, and the orientation of the femur is sampled. Second position data which define a position of the leg, and therefore of the femur, at the second point in time are also obtained. In this embodiment, the expression "position of the leg" means the rotational alignment of the femur about the centre of rotation of the femoral head. The second landmark vector is only determined if the second position data match the neutral position data. In other words, the second landmark vector can only be determined if the femur is in the same position at both the first and second points in time. In this embodiment, the word "match" can mean that the position data are exactly identical but may also include an allowable deviation between the position of the femur at the first and second points in time of for example up to 1, 2, 5 or 10 degrees.

The neutral position of the leg, and thus of the femur, relative to the pelvis refers to a position of the leg when the patient is standing at a normal angle and with a normal base of gait, which is widely used as a reference position for assessing deviations from the norm. The neutral position is well known in medical practice.

In this embodiment, the position data are preferably acquired from an inertial sensor. The inertial sensor determines its orientation in a co-ordinate system such as the global co-ordinate system. The inertial sensor is preferably attached to the thigh which is to be examined. The inertial sensor can for example be attached using tape or bandaging.

In one embodiment of the invention, a landmark vector is calculated from two landmark reference vectors, wherein each landmark reference vector represents a vector between the respective landmark and a common reference point. The two landmarks and the common reference point generally constitute a triangle. The two landmark reference vectors constitute two known sides of the triangle, and the angle between these sides is known, such that the length and direction of the third side, which together characterise the landmark vector, can be calculated.

At least one of the landmark reference vectors is determined using a light beam which is emitted from a light beam source and pointed at an offset point. The light beam is in particular a light beam in the visible spectrum, preferably a laser beam. The light beam source has a known distance from the landmark and a known orientation relative to the direct line from the light source to the landmark. This means that the angle between the light source and the shortest (direct) line from the light source to the landmark is known.

This can be achieved by attaching the light source to a pointer which comprises a tip for touching the landmark. In this case, the distance between the light source and the tip of the pointer and the orientation of the light source relative to the pointer are known. Alternatively, a laser range finder is attached to the light source. The laser beam of the laser range finder is pointed at the landmark, wherein the relative position between the light beam source and the laser range finder is known. This known relative position and the distance determined using the laser range finder can be used to determine or calculate the distance between the light source and the landmark and the orientation of the light source relative to the direct line from the light source to the landmark. Any distances relating to the light beam source are preferably determined relative to a light beam source reference point of the light beam source.

Determining a landmark reference vector also involves acquiring the direction of the light beam and the distance between the light beam source (preferably the light beam source reference point) and the offset point. The landmark reference vector is then calculated from the known distance between the light source and the landmark, the known orientation of the light source relative to the direct line from the light source to the landmark, the direction of the light beam, the distance between the light beam source and the offset point, and the reference offset between the offset point and the reference point.

In this approach, a quadrilateral is defined by the landmark, the light source (preferably defined by the light beam source reference point), the offset point and the reference point. Since the orientation and length of three of the sides of the quadrilateral are known, the direction and the length of the fourth side, which is the landmark vector, can be calculated.

In one embodiment, the landmark reference vector between the second landmark and the common reference point is only determined once and is used for determining both the first landmark vector and the second landmark vector. This is in particular possible if the relative position between the second landmark and the common reference point is identical at the first and second points in time.

The common reference point has a constant position in the co-ordinate system which remains constant while a landmark vector, i.e. the first or second landmark vector, is determined. However, the position of the common reference point can change between the point in time at which the first landmark vector is determined and the point in time at which the second landmark vector is determined. The position of the offset point can also vary for each determination of a landmark reference vector. This means that the offset point can be different for each landmark reference vector.

The reference point and the offset point are preferably points on a reference device. The reference device is static in the global co-ordinate system, at least during the period of time required to determine all the necessary data such as the landmark reference vectors. The reference device can for example be a pole or other structure which has a spatially extended surface. The reference device preferably comprises at least one label or surface structure with the aid of which the distance between the offset point and the reference point can be determined.

In one embodiment, the reference offset is determined from an image depicting the reference device. The reference point and the offset point can be identified in this image. The offset point is the point at which the light beam is reflected by the reference device. The reference offset can be determined on the basis of known properties of the camera used to capture the image. The distance between the offset point and the reference point can for example be calculated from the distance between the offset point and the reference point in the image. This distance can alternatively or additionally be calculated from the label on the reference device or the structure of the reference device. The camera which captures the image of the reference device can be attached to the light beam source or can be provided independently. Attaching the camera to the light beam source has the advantage that the relative orientation between the camera and the light beam source is known, such that the orientation of the camera, and therefore the orientation of the image, in the global co-ordinate system can be calculated from the orientation of the light beam source.

The reference offset is preferably determined from the orientation of the reference device in the global co-ordinate system. This orientation can be known, for example because it is vertical, or can be measured using an orientation sensor such as a gyroscope. The reference offset is then preferably calculated in the global co-ordinate system from the distance between the offset point and the reference point, the orientation of the reference device and the known location of the offset point on the reference device.

In one embodiment, the reference offset is zero, i.e. the light beam points directly at the reference point. The quadrilateral thus becomes a triangle defined by the landmark, the light beam source and the reference point.

In this embodiment, a light beam detector is preferably arranged at the reference point and detects whether or not the light beam hits the reference point. If it does, a measurement of the orientation of the light beam source and the distance between the light beam source and the reference point is automatically triggered.

In the embodiments described thus far, the second landmark is preferably a pelvic landmark on the pelvis of the patient. The pelvic landmark is in particular a point of the pelvis. The second landmark is thus preferably a natural landmark, i.e. a point on the pelvic bone, or an artificial landmark such as for example a reference which is pre-inserted into the pelvic bone.

In another embodiment, the second landmark is a virtual landmark, namely the centre of rotation of the pelvis. The centre of rotation of the pelvis is the centre of the acetabulum and therefore identical to the centre of the femoral head. Such a virtual landmark cannot be sampled directly, for example using a pointer or a laser range finder as described above. The landmark vector between the femoral landmark and the virtual landmark therefore has to be determined differently, in particular by an indirect approach.

In this embodiment, this landmark vector is determined as the average of two auxiliary landmark vectors, wherein each auxiliary landmark vector represents a vector between an auxiliary landmark and the femoral landmark. An auxiliary landmark can be an actual landmark or an artificial landmark as described above. Preferably, all the auxiliary landmarks are points on the acetabular rim of the pelvis. The centre of rotation of the femur is assumed to be located centrally between the two auxiliary landmarks.

If a landmark vector is calculated from two landmark reference vectors as described above and the second landmark is a virtual landmark, then the corresponding landmark reference vector is a virtual landmark reference vector for the virtual landmark, i.e. a vector between the virtual landmark and the reference point. The virtual landmark reference vector is determined as the average of two auxiliary reference vectors, wherein each auxiliary reference vector represents a vector between one of the auxiliary landmarks and the common reference point.

Each of the two auxiliary reference vectors is determined in the same way as a landmark reference vector as described above, but with the respective auxiliary landmark replacing the second landmark. This means that the light beam source has a known distance from the auxiliary landmark and a known orientation relative to a direct line from the light source to the auxiliary landmark. All the other steps are likewise performed as described above.

In an alternative, which might be considered as a self-contained invention, a first mechanical axis vector between the virtual landmark (i.e. the centre of rotation of the acetabulum) and a patellar landmark is acquired for the position of the femur at the first point in time. This is the position of the femur when the data for determining the first landmark vector are acquired. The patellar landmark is a landmark on the patella and can be a natural or an artificial landmark, as described above. The leg length direction at the first point in time is then the direction of the first mechanical axis vector, and the leg offset is the distance of the femoral landmark from the mechanical axis, which is represented by the first mechanical axis vector. The leg offset direction is thus the direction of a line which is perpendicular to the first mechanical axis vector and runs through the femoral landmark. If the femur is in the same position relative to the pelvis at the first and second point in time, then the leg length difference and the leg offset difference can be calculated based on the leg length direction and the leg offset direction.

The first mechanical axis vector can be determined directly or using a reference point as described above. In particular, a first patellar reference vector between the patellar landmark and the common reference point is determined. A virtual landmark reference vector between the virtual landmark and the reference point is determined as described above. The first mechanical axis vector is then calculated from the virtual landmark reference vector and the first patellar reference vector.

In one embodiment, a second mechanical axis vector between the virtual landmark (i.e. the centre of rotation of the acetabulum) and the patellar landmark is acquired for the position of the femur at the second point in time. This is the position of the femur when the data for determining the second landmark vector are acquired. The leg length direction at the second point in time is then the direction of the second mechanical axis vector, and the leg offset direction is the direction of a line which is perpendicular to the leg length direction and runs through the femoral landmark.

The second mechanical axis vector can be determined directly or using a reference point as described above. In particular, a second patellar reference vector between the patellar landmark and the common reference point is determined. A virtual landmark reference vector between the virtual landmark and the reference point is determined as described above. The second mechanical axis vector is then calculated from the virtual landmark reference vector and the second patellar reference vector.

The difference between the directions of the two mechanical axis vectors represents a rotation of the femur about the centre of rotation of the acetabulum, between the first and second points in time. If the position of the femur relative to the pelvis has changed between the first and second points in time, then this change in the relative position has to be considered.

In one embodiment, the leg length and the leg offset at the first point in time are calculated based on the leg length direction and the leg offset direction at the first point in time. The leg length and the leg offset at the second point in time are calculated based on the leg length direction and the leg offset direction at the second point in time. The leg length difference is then calculated as the difference of the leg lengths at the first and second points in time and the leg length offset is then calculated as the difference of the leg offsets at the first and second points in time.

In another embodiment, a rotational transformation which transforms the direction of the second mechanical axis vector into the direction of the first mechanical axis vector is calculated, and this rotational transformation is applied to the second landmark vector before the leg length difference and the leg offset difference are calculated. Applying the rotational transformation to the second landmark vector compensates for a rotation of the femur between the first and second points in time. This has the advantage that the first and second landmark vectors do not require the femur to be in the same rotational position relative to the pelvis at both points in time.

It shall be noted that this transformation can also be used in combination with the first embodiments of the invention in which the leg length direction is calculated by projecting the first landmark vector into a sagittal plane. In this case, the second landmark vector is transformed using the rotational transformation in order to make it comparable to the first landmark vector.

Determining a vector, such as a landmark vector or a landmark reference vector, in particular means determining vector data which represent the length and/or direction of the vector. Acquiring a direction in particular means acquiring direction data which represent the direction. Acquiring a distance in particular means acquiring distance data which represent the distance.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The present invention also relates to a computer on which the aforementioned program is stored or executed.

The present invention also relates to a device for determining a leg length difference and a leg offset of a patients leg including a femur. The device comprises a computer as described above.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). A computer as referred to herein is a technical computer which in particular comprises technical, in particular tangible components, in particular mechanical and/or electronic components. Any device mentioned herein is a technical and in particular tangible device.

The method in accordance with the invention is in particular a data processing method. The data processing method is preferably performed using technical means, in particular a computer. The data processing method is preferably designed to be executed by or on a computer and is in particular executed by or on the computer. All the steps or merely some of the steps (i.e. less than the total number of steps) of the method in accordance with the invention can in particular be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of technical data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the tem "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. An example of a display device is an augmented reality device (also called augmented reality glasses) which may be used as "goggles" for navigating. A specific example of such augmented reality glasses is Google Glass (trademark of Google Inc.). An augmented reality device may be used both to input information into the computer by user interaction and to display information outputted by said computer.

The expression "acquiring data" or "obtaining data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention in particular does not involve, comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for fastening the medical implant to it. More specifically, the invention does not involve, comprise or encompass any surgical or therapeutic activity. For this reason alone, no surgical or therapeutic activity and in particular no surgical or therapeutic step is necessitated or implied by carrying out the invention.

Figure 2:
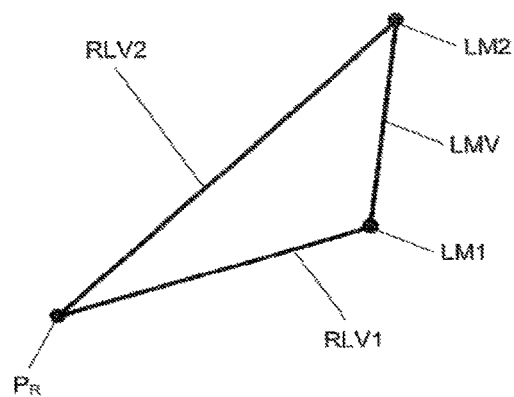
Figure 3:
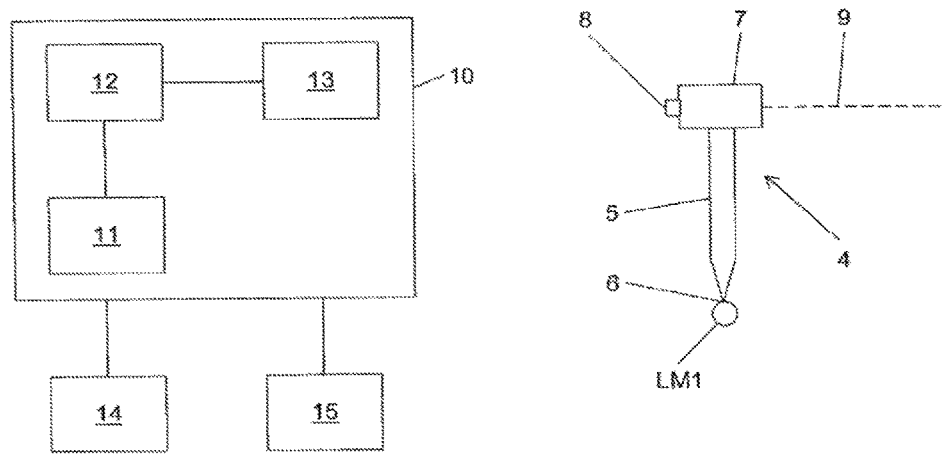
Figure 4:
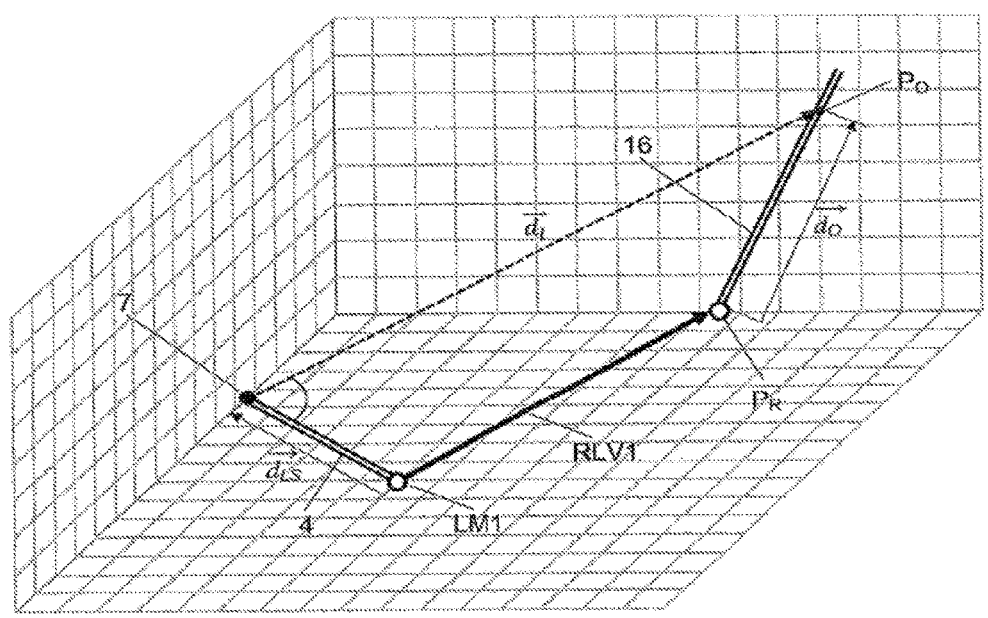
Figure 5:
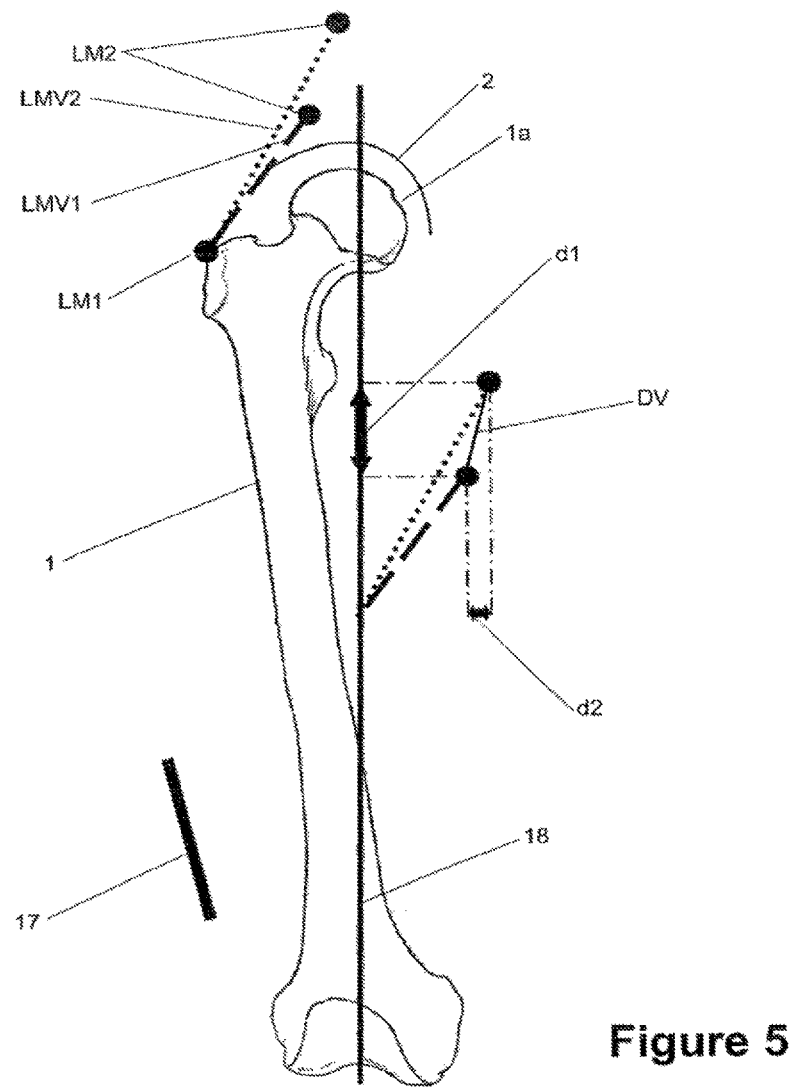
Figure 6:
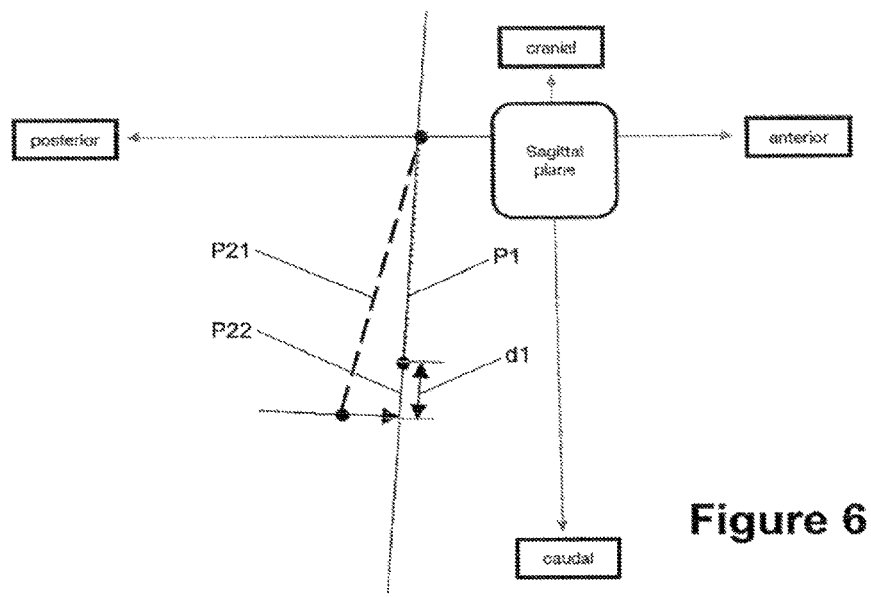
Figure 7:
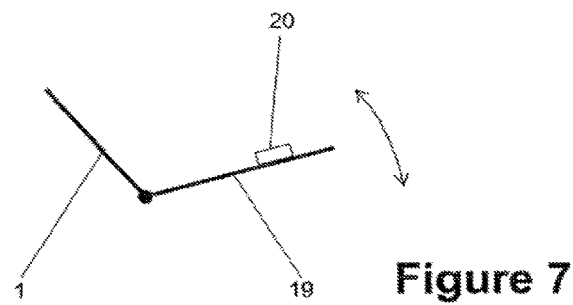
Figure 8:
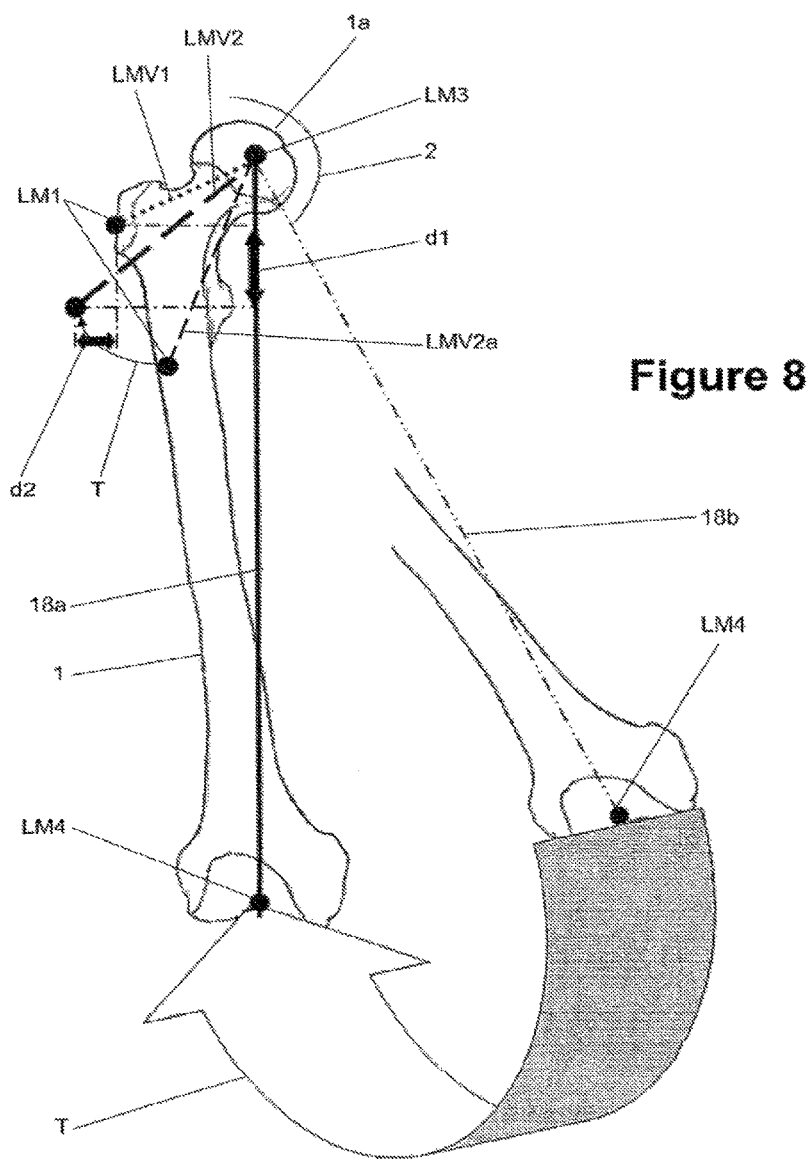
Figure 9:
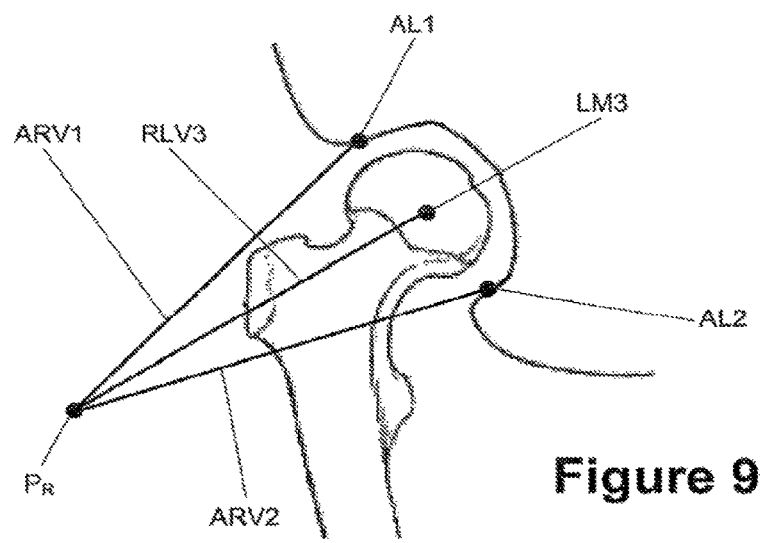

The invention and potential alternatives shall now be explained in more detail with reference to the accompanying drawings, which show:

FIG. 1 a femur at two different points in time;

FIG. 2 a geometry of two landmarks and a reference point;

FIG. 3 a system for determining a landmark vector, including a registration tool;

FIG. 4 a geometry for determining a landmark vector;

FIG. 5 a first example of determining the leg length difference and the leg offset difference;

FIG. 6 a geometry for determining the leg length difference;

FIG. 7 an example of determining the orientation of a sagittal plane;

FIG. 8 a second example of determining the leg length difference and the leg offset difference; and FIG. 9 an example of determining a virtual landmark.

FIG. 1 shows a femur 1 at two different points in time. The femur 1 comprises a femoral shaft and a femoral head 1a which are connected by a femoral neck. The femoral head 1a rests in a socket, the acetabulum, of the pelvis 2. The femoral head 1a is located at the proximal end of the femur 1. At its distal end, the femur 1 comprises a medial condyle, a lateral condyle and an intercondylar notch between them. The distal end of the femur 1 is connected to a tibia (not shown) via the knee joint.

FIG. 1 also shows a sagittal plane 3 which is perpendicular to the plane of the drawing. The sagittal plane extends in an up-down (superior-inferior or cranial-caudal) direction and in a front-back (anterior-posterior or ventral-dorsal) direction relative to the patient's body. The mechanical axis of the femur 1, which runs through the centre of the femoral head 1a and the centre of the intercondylar notch, lies approximately within the sagittal plane 3.

FIG. 1 also shows a global co-ordinate system GCS which is an earth-fixed co-ordinate system. Orientations (also referred to as directions) of lines or vectors are determined or measured in this global co-ordinate system.

The structure of the femur 1 has changed between the first and second points in time—in particular, the femoral neck has become longer. The structural change in the femur 1 is illustrated in an exaggerated manner in order to emphasise it in the drawings.

FIG. 1 also shows two landmarks LM1 and LM2. The landmark LM1 is a point on the greater trochanter of the femur 1, and the landmark LM2 is a point on the acetabular rim of the socket of the pelvis 2. The landmark LM1 is also referred to as the femoral landmark, and the landmark LM2 is an example of a second landmark.

A vector between the two landmarks LM1 and LM2 is referred to as a landmark vector. The position of the landmark LM1 relative to the landmark LM2 changes between the first point in time and the second point in time, because the structure of the femur 1 and/or pelvis 2 has changed, hence the landmark vector also changes between the first point in time and the second point in time. The landmark vector at the first point in time is referred to as LMV1, and the landmark vector at the second point in time is referred to as LMV2.

In the present invention, a landmark vector is not determined by acquiring the exact locations of the landmarks in the global co-ordinate system and determining the landmark vector from the difference between the locations. Only the directions and the lengths of the landmark vectors LMV1 and LMV2 are used in order to calculate the leg length difference and the leg offset difference. Methods for determining the landmark vectors include a direct measurement or a determination from medical image data, such as CT or MR image data.

As an option, a landmark vector can be determined from two landmark reference vectors between the respective landmark and a common reference point. The principle of this approach is shown in FIG. 2.

As shown in FIG. 2, the two landmarks LM1 and LM2 and the common reference point $P_R$ constitute the corners of a triangle. The landmark vector LMV is represented by the side of the triangle between the landmarks LM1 and LM2. The landmark reference vector between the landmark LM1 and the common reference point $P_R$ is referred to as RLV1, and the landmark reference vector between the landmark LM2 and the common reference point $P_R$ is referred to as RLV2. Once the two landmark reference vectors RLV1 and RLV2 are known, for example by being measured, then the landmark vector LMV can be calculated.

In an exceptional case, the two landmarks LM1 and LM2 and the common reference point $P_R$ may all lie on one line. In this case, the three points do not constitute a triangle. However, the landmark vector LMV can still be calculated from the two landmark reference vectors RLV1 and RLV2.

FIG. 3 schematically shows a system for determining a landmark vector. The system comprises a registration tool 4 and a medical navigation system 10.

The registration tool 4 comprises a body 5 featuring a landmark point 6 which is to be held against a landmark, such as for example the landmark LM1 as shown in FIG. 3. A light beam source 7 which is capable of emitting a light beam 9 is rigidly attached to the body 5. The location and orientation of the light beam source 7 on the body 5 is known, such that the distance between the light beam source 7 and the landmark point 6 and the direction of the light beam 9 relative to the body 5 is known. An orientation sensor 8 for determining the orientation of the registration tool 4 in the global co-ordinate system is rigidly attached to the registration tool 4. If the global co-ordinate system is an earth-fixed co-ordinate system, then the orientation sensor 8 can for example be an inertial sensor such as a three-axis gyroscope. The orientation sensor 8 is capable of transmitting the determined orientation to the medical navigation system 10.

The medical navigation system 10 comprises a receiving unit 11 for receiving the orientation of the registration tool 4 from the orientation sensor 8, and a central processing unit 12 which is adapted to run a program which implements the method described herein and is connected to the receiving unit 11 in order to receive the orientation of the registration tool 4 from the receiving unit 11. The central processing unit 12 is also connected to a memory device 13 in which the program and/or data for performing the method is/are stored.

The navigation system 10 also comprises an input unit 14 for receiving information and an output unit 15 for displaying information.

The principle of determining a landmark direction shall now be explained with reference to FIG. 4. As shown in this figure, the landmark point 6 of the registration tool 4 is held at the landmark LM1, and a reference device 16 is provided in such a way that it is static in the global co-ordinate system GCS. The orientation of the reference device 16 is either known and provided to or stored in the medical navigation system 10 or is determined using an orientation sensor (not shown) and sent to the medical navigation system 10. The reference point $P_R$ is defined on the reference device 16.

In the present example, the light beam source 7 is a laser range finder which is capable of determining the distance between the laser range finder 7 and a point at which the laser beam 9 is reflected. It is also capable of transmitting the determined distance to the medical navigation system 10 via the receiving unit 11.

The registration tool 4 is held such that the light beam 9 hits the reference device 16. The point at which the light beam 9 hits the reference device 16 and is reflected back to the registration tool 4 is referred to as the offset point $P_O$. Since the orientation of the light beam source 7 can be measured using the orientation sensor 8, and the distance between the offset point $P_O$ and the light beam source 7 can be measured, the medical navigation system 10 can calculate the vector $d_1$ from the light beam source 7 to the offset point $P_O$. The light beam source 7, the landmark LM1, the offset point Po and the reference point $P_R$ constitute a quadrilateral, as can be seen from FIG. 4. The vector RLV1 from the landmark LM1 to the reference point $P_R$ is the landmark reference vector which is associated with the landmark LM1. This vector can be calculated if enough information about the quadrilateral is available.

The vector $d_{LS}$ from the landmark LM1 to the light source 7 can be calculated from the known relative position between the light source 7 and the landmark point 6 in combination with the orientation of the registration tool 4 as determined using the orientation sensor 8. The offset vector $d_O$ can be calculated from the orientation of the reference device 16 and the location of the offset point $P_O$ on the reference device 16. This location can be determined automatically, for example by a camera which captures an image of the reference device 16 and calculates the location by identifying the offset point $P_O$ in the image, or manually by an operator who identifies the location of the offset point $P_O$ on the reference device 16 and inputs this information into the medical navigation system 10 using the input unit 14.

Once the vectors $d_{LS}$, $d_1$ and $d_O$ are known, the vector RLV1 representing the landmark reference vector of the first landmark LM1 can be calculated.

As compared to the illustration in FIG. 1, the two landmark vectors LMV1 and LMV2 in FIG. 5 have the landmark LM1 in common (as a start or end point) instead of the landmark LM2. These two illustrations are equivalent because both correctly represent the shift between the landmarks LM1 and LM2 from the first point in time to the second point in time.

As in FIG. 1, so also FIG. 5 shows the femur 1 with its femoral head 1a in the socket of the pelvis 2. FIG. 5 also shows the mechanical axis 18 of the femur 1. This mechanical axis 18 runs through the centre of rotation of the femoral head 1a and the intercondylar notch. The leg length difference is defined in the direction of the mechanical axis 18, while the direction of the leg offset, i.e. a lateral shift of the femoral shaft between the first and second points in time, is defined in a lateral direction which is perpendicular to the mechanical axis 18 and runs through the femoral landmark LM1.

In order to determine the leg length difference and the leg offset difference, the relative shift between the landmark LM1 and the landmark LM2 from the first point in time to the second point in time has to be separated or decomposed into a component in the leg length direction and a component in the leg offset direction. In FIG. 5, this shift is represented by a difference vector DV. In the example shown in FIG. 5, the difference vector DV is decomposed into the leg length difference d1 and the leg offset difference d2.

As outlined above, some embodiments assume that the leg offset direction is perpendicular to the sagittal plane 3. It is then necessary to determine the orientation of the sagittal plane 3. Two different approaches for determining the orientation of the sagittal plane are given below. In addition, it is apparent from FIG. 5 that the relative shift between the landmark LM1 on the femur and the landmark LM2 on the pelvis depends not only on the structural change in the femur 1 but also on a changed rotational alignment between the femur 1 and the pelvis 2. In order to correctly determine the leg length difference and the leg offset difference from the two landmark vectors LMV1 and LMV2, it is necessary to ensure that there is no such change in the rotational alignment or that any change in the rotational alignment is compensated for. Both approaches are described below.

A detailed description of how the leg length difference d1 is determined according to the present invention, that is using a sagittal plane 3 as shown in FIG. 1, shall now be given with reference to FIG. 6. In this figure, the sagittal plane 3 is equivalent to the plane of the drawing. The line P1 is the orthogonal projection of the first landmark vector LMV1 into the sagittal plane 3, while the line P21 is the first orthogonal projection of the second landmark vector LMV2 into the sagittal plane 3. If the change in the structure of the femur 1 also shifts the femoral shaft in the anterior-posterior direction, then the directions of the lines P1 and P21 are not identical. The anterior-posterior difference between the first landmark vector LMV1 and the second landmark vector LMV2 is irrelevant for calculating the leg length difference. A second line P22 is then calculated as an orthogonal projection of the first projection (line P21) of the second landmark vector LMV2 into the sagittal plane 3 and onto the line P1. In an alternative, the line P21 is rotated onto the line P1 instead. The directions of the lines P1 and P22 are then identical, and the leg length difference d1 is calculated as the difference in length between the lines P1 and P22.

A first approach for determining the orientation of the sagittal plane 3 assumes that the patient is in a lateral recumbent position at both the first and second points in time. It is then assumed that the sagittal plane 3 is a horizontal plane. In a second approach, an orientation sensor is used to determine the orientation of the surface on which the patient lies, such as for example the surface of an operating table. This orientation is determined in the global co-ordinate system GCS and provided to the medical navigation system 10.

Another approach for determining the orientation of the sagittal plane 3 is illustrated in FIG. 7. FIG. 7 shows the femur 1 connected to the tibia 19 via a knee joint. The femur 1 is locked in position, preferably in its neutral position, relative to the pelvis 2. The tibia 19 is then flexed and/or extended relative to the femur 1, as indicated by the arrow in FIG. 7. An orientation sensor 20 attached to the tibia 19 then samples a plurality of orientation datasets for different alignments between the femur 1 and the tibia 19. The plane in which the orientation sensor 20, and therefore the tibia 19, moves can be calculated from these orientation datasets. The orientation of this plane is then used as the orientation of the sagittal plane 3.

One approach for ensuring that the relative orientation, i.e. the rotational alignment, between the femur 1 and the pelvis 2 is identical at the first and second points in time uses an orientation sensor 17 attached to the patient's leg, as indicated in FIG. 5. In the example illustrated in FIG. 5, the orientation sensor 17 is attached to the soft tissue of the patient, for example using adhesive tape or bandaging. The orientation sensor 17 determines its orientation within the global co-ordinate system GCS at the first point in time and transmits this to the medical navigation system 10.

Before the second point in time, the orientation sensor 17 intermittently or continuously determines its orientation in the global co-ordinate system GCS and transmits this to the medical navigation system 10, where it is displayed on the display unit 15. The orientation of the femur 1 relative to the pelvis 2 can then be adjusted until the orientation of the orientation sensor 17 in the global co-ordinate system GCS matches its orientation at the first point in time, wherein a match can be deemed to have been achieved if the difference with respect to the orientation at the first point in time is below a predetermined threshold. The medical navigation system 10 can optionally indicate on the display unit 15 whether or not the orientations of the orientation sensor 17 match.

Additionally or alternatively, the medical navigation system 10 can sample the data from the registration tool 4 at the second point in time only, if the orientations of the orientation sensor 17 match.

The orientation sensor 17 can be any orientation sensor, such as for example a gyro sensor, which is capable of transmitting the raw sensor output data or the orientation in the global co-ordinate system to the medical navigation system 10. One example of a device which contains such an orientation sensor is an iPod such as is produced by Apple, Inc.

One approach for compensating for a change in the rotational alignment between the femur 1 and the pelvis 2 between the first and second points in time is illustrated in FIG. 8. The position of the femur 1 at the first point in time is shown by the complete representation of the femur 1 exhibiting the mechanical axis 18a. The position of the femur 1 relative to the pelvis 2 at the second point in time is indicated by the partial representation of the femur 1 exhibiting the mechanical axis 18b. The landmark, vector LMV1 is determined at the first point in time, and the landmark vector LMV2a is determined at the second point in time.

The mechanical axes 18a and 18b are determined from the landmark LM3 and the landmark LM4. The landmark LM3 is the centre of rotation of the femoral head 1a, which coincides with the centre of rotation of the acetabulum, and is thus a virtual landmark which cannot be accessed directly. The landmark LM4 is a point on the intercondylar notch or on the patella and can therefore be referred to as the patellar landmark. The landmark vectors representing the mechanical axes 18a and 18b can be determined using landmark reference vectors between the landmark LM3 or LM4, respectively, and a common reference point such as for example the common reference point $P_R$, in the same way as has already been described above. A rotational transformation T is then calculated which transforms the direction of the mechanical axis 18b into the direction of the mechanical axis 18a, in particular about the landmark LM3, i.e. the centre of rotation of the acetabulum. This rotational transformation T is then applied to the second landmark vector LMV2a, resulting in a transformed second landmark vector LMV2. The leg length difference and the leg offset can then be calculated from the two landmark vectors LMV1 and LMV2, as described above.

As outlined above, the virtual landmark LM3 cannot be accessed directly using the registration tool 4. An indirect approach to determining a reference landmark vector for a virtual landmark shall accordingly now be described with reference to FIG. 9.

This approach uses two auxiliary landmarks AL1 and AL2 on the acetabular rim of the pelvis 2. The centre of rotation of the acetabulum, and therefore the virtual landmark LM3, is considered to be halfway between the two auxiliary landmarks AL1 and AL2. In order to determine the landmark reference vector RLV3 between the virtual landmark LM3 and the common reference point $P_R$, a first auxiliary landmark reference vector ARV1 between the auxiliary landmark AL1 and the common reference point $P_R$ and a second auxiliary landmark reference vector ARV2 between the second auxiliary landmark AL2 and the common reference point $P_R$ are determined. The reference landmark vector RLV3 is then calculated as the average of the first auxiliary landmark reference vector ARV1 and the second auxiliary landmark reference vector ARV2.

As an alternative, the mechanical axes 18a and 18b can be determined by acquiring the vectors, or at least the directions of the vectors, between the landmark LM4 and the two auxiliary landmarks AL1 and AL2, respectively, and then calculating the direction of a mechanical axis as the average of the two directions of said vectors.

As an alternative to the approach of using projections of the landmark vectors into a sagittal plane for determining the leg length direction, the directions of the mechanical axes 18a and 18b can be used as the leg length directions at the first and second point in time, respectively. In one embodiment, the transformation is applied to the second landmark vector LMV2 as described above, such that the leg length directions for the first landmark vector LMV1 and the transformed second landmark vector LMV2 are identical. The two landmark vectors thus become directly comparable.

In another embodiment, the first landmark vector LMV1 is decomposed into components in the leg length direction and the leg offset direction based on the direction of the mechanical axis 18a and the second landmark LMV2 is decomposed based on the direction of the mechanical axis 18b. The corresponding components of the two landmark vectors are then compared to calculate the leg length difference and the leg offset difference.

The invention claimed is:

1. A method for analysing images, performed by a computer, through analysis of medical image data, comprising the steps of:
obtaining medical image data from a medical imaging device, the medical imaging device generating at least a CT or MR medical image data during a scan of a patient's femur connected to a patient's pelvis;
measuring, by the computer, a first landmark vector between a femoral landmark and a second landmark at a first point in time from the medical image data;
measuring, by the computer, a second landmark vector between the femoral landmark and the second landmark at a second point in time which is later than the first point in time from the medical image data;
calculating, by the computer, an orthogonal projection of the first landmark vector into a sagittal plane and using the direction of the orthogonal projection of the first landmark vector into the sagittal plane as an element length direction;
calculating, by the computer, a direction which is perpendicular to the sagittal plane and using the calculated direction perpendicular to the sagittal plane as an element offset direction;
calculating, by the computer, the element length difference in the element length direction and the element offset difference in the element offset direction from the first landmark vector and the second landmark vector;
preparing, by the computer, for presentation and output on a display unit of a medical navigation system the calculated element length difference and using the calculated element length difference in the medical navigation system.

2. A method, performed by a computer, for measuring a leg length difference and a leg offset difference of a patient's leg including a femur connected to a pelvis, comprising the steps of:
measuring, by a registration tool operably connected to a computer, a first landmark vector between a femoral landmark and a second landmark at a first point in time;
transmitting from the registration tool to an input unit of the computer in a medical navigation system, the measurement values of the first landmark vector;
measuring by the registration tool operably connected to the computer, a second landmark vector between the femoral landmark and the second landmark at a second point in time which is later than the first point in time;
transmitting from the registration tool to the input unit of the computer in the medical navigation system, the measurement values of the second landmark vector;
calculating, by the computer, an orthogonal projection of the first landmark vector into a sagittal plane and using the direction of the orthogonal projection of the first landmark vector into the sagittal plane as a leg length direction;

calculating, by the computer, a direction which is perpendicular to the sagittal plane and using this direction as a leg offset direction; and calculating, by the computer, the leg length difference in the leg length direction and the leg offset difference in the leg offset direction from the first landmark vector and the second landmark vector;

preparing, by the computer, for presentation and output on a display device connected to the medical navigation computer the calculated leg length difference and using the calculated leg length difference in the medical navigation system.

3. The method according to claim 2, wherein an orientation of the sagittal plane is defined as being horizontal.

4. The method according to claim 2, wherein an orientation of the sagittal plane is determined as the orientation of a surface of an operating table on which the patient is located.

5. The method according to claim 2, wherein an orientation of the sagittal plane is determined from a plurality of inertial sensor data which are acquired from an inertial sensor attached to the tibia of the leg while the femur is locked in position and the tibia is flexed relative to the femur.

6. The method according to claim 4, wherein a first sagittal plane is determined for the first landmark vector, and a second sagittal plane is determined for the second landmark vector, and orthogonal projections of the landmark vectors into the corresponding sagittal plane are calculated.

7. The method according to claim 2, wherein calculating the leg length difference and the leg offset difference involves calculating a first orthogonal projection of the second landmark vector into the sagittal plane, calculating a second orthogonal projection of the first orthogonal projection onto the projection of the first landmark vector, determining the leg length difference as the difference in length between the projection of the first landmark vector and the second projection of the second landmark vector, and calculating the leg offset difference as the difference between the components of the first landmark vector and the second landmark vector in the leg offset direction.

8. The method according to claim 2, wherein calculating the leg length difference and the leg offset difference involves calculating an orthogonal projection of the second landmark vector into the sagittal plane, rotating the orthogonal projection of the second landmark vector within the sagittal plane such that its direction matches the direction of the projection of the first landmark vector, determining the leg length difference as the difference in length between the projection of the first landmark vector and the rotated second landmark vector, and calculating the leg offset difference as the difference between the components of the first landmark vector and the second landmark vector in the leg offset direction.

9. The method according to claim 2, wherein calculating the leg length difference and the leg offset difference involves calculating a difference vector between the first landmark vector and the second landmark vector and decomposing the difference vector into its components in the leg length direction and the leg offset direction.

10. The method according to claim 2, comprising the steps of obtaining neutral position data which define a neutral position of the leg at the first point in time and obtaining second position data which define a position of the leg at the second point in time, wherein the second landmark vector is only determined if the second position data match the neutral position data.

11. The method according to claim 10, wherein the position data are acquired from an inertial sensor.

12. The method according to claim 2, wherein the first and second landmark vectors are calculated from two landmark reference vectors, wherein each landmark reference vector represents a vector between the respective landmark and the reference point common to the femoral and second landmarks and at least one of the landmark reference vectors is determined using a light beam which is emitted from a light beam source and pointed at an offset point, the light beam source having a known distance from the landmark and a known orientation relative to the direct line from the light source to the landmark, determining the first and second landmark vectors, including acquiring the direction of the light beam and the distance between the light beam source and the offset point, and calculating the landmark reference vector from the known distance between the light source and the landmark, the known orientation of the light source relative to the direct line from the light source to the landmark, the direction of the light beam, the distance between the light beam source and the offset point and the reference offset between the offset point and the reference point.

13. The method according to claim 12, wherein the second landmark is a virtual landmark, being the center of rotation of the acetabulum; one of the landmark reference vectors is a virtual landmark reference vector for the virtual landmark and is determined as the average of two auxiliary reference vectors, wherein each auxiliary reference vector represents a vector between an auxiliary landmark and the common reference point and comprising the steps of obtaining neutral position data which define a neutral position of the leg at the first point in time and obtaining second position data which define a position of the leg at the second point in time, wherein the second landmark vector is only determined if the second position data match the neutral position data,
wherein the position data are acquired from an interior sensor, and
wherein the respective auxiliary landmark is used as the landmark.

14. A non-transitory computer-readable storage medium storing a program which, when running on a computer, causes the computer to perform the steps of
determining by a registration tool connected to a computer, a first landmark vector between a femoral landmark and a second landmark at a first point in time;
receiving from the registration tool to an input unit of the computer of a medical navigation system, the measurement values of the first landmark vector;
determining a second landmark vector between the femoral landmark and the second landmark at a second point in time which is later than the first point in time;
receiving from the registration tool to the input unit of the computer on the medical navigation system, the measurement values of the second landmark vector;
calculating, by the computer, an orthogonal projection of the first landmark vector into a sagittal plane and using the direction of the orthogonal projection of the first landmark vector into the sagittal plane as a leg length direction;
calculating, by the computer, a direction which is perpendicular to the sagittal plane and using this direction as a leg offset direction; and calculating, by the computer, the leg length difference in the leg length direction and the leg offset difference in the leg offset direction from the first landmark vector and the second landmark vector;

preparing, by the computer, for presentation and output on a display device connected to the computer the calculated leg length difference and using the calculated leg length difference in the medical navigation system.

15. A device for determining a leg length difference and a leg offset difference of a patient's leg including a femur connected to a pelvis, comprising a computer that executes a program that causes the computer to obtain medical image data from a medical imaging device, the medical imaging device generating at least CT or MR medical image data during a scan of a patient's femur connected to a patient's pelvis;

determine, by the computer, a first landmark vector between a femoral landmark and a second landmark at a first point in time;

determine, by the computer, a second landmark vector between the femoral landmark and the second landmark at a second point in time which is later than the first point in time;

calculate, by the computer, an orthogonal projection of the first landmark vector into a sagittal plane and use the direction of the orthogonal projection of the first landmark vector into the sagittal plane as a leg length direction;

calculate, by the computer, a direction which is perpendicular to the sagittal plane and use this direction as a leg offset direction; and calculate, by the computer, the leg length difference in the leg length direction and the leg offset difference in the leg offset direction from the first landmark vector and the second landmark vector;

transmit, by the computer, for presentation to an output unit of a medical navigation system the calculated leg length difference and using the calculated leg length difference in the medical navigation system.

* * * * *